(12) United States Patent
Park et al.

(10) Patent No.: US 8,043,380 B1
(45) Date of Patent: Oct. 25, 2011

(54) BONE IMPLANT WITH OSTEO-INDUCING STRUCTURE

(75) Inventors: Ilwhan Park, Walnut Creek, CA (US); Janzen Lo, Allentown, PA (US); Jeffrey Kozak, Houston, TX (US); Oliver Burckhardt, Bethlehem, PA (US)

(73) Assignee: Aesculap Implant Systems, LLC., Center Valley, PA (US)

( * ) Notice: Subject to any disclaimer, the term of this patent is extended or adjusted under 35 U.S.C. 154(b) by 1992 days.

(21) Appl. No.: 10/633,271

(22) Filed: Jul. 31, 2003

(51) Int. Cl.
*A61F 2/44* (2006.01)

(52) U.S. Cl. .................................................. 623/17.16

(58) Field of Classification Search ..... 623/17.11–17.16
See application file for complete search history.

(56) References Cited

U.S. PATENT DOCUMENTS

| 6,716,247 B2* | 4/2004 | Michelson | 623/17.16 |
| 7,037,339 B2* | 5/2006 | Houfburg | 623/17.11 |

* cited by examiner

*Primary Examiner* — Anu Ramana
(74) *Attorney, Agent, or Firm* — RatnerPrestia

(57) ABSTRACT

A spine implant system having two or more adjacent segments that have a male-female annular interlocking relationship for increased mechanical stability and resistance to relative translation and rotation. One or more segments is provided with at least one perforation channel or void to promote osteo-induction within the segment. Optionally, two adjacent segments have at least one common or aligned perforation channel or void. Two or more spaced apart portions of a segment surface are optionally chamfered to provide easier fabrication and/or positioning of the segment. Two spaced apart exposed surface planes of an interlocked segment pair optionally are axially oriented at a small positive angle relative to each other, to approximate natural spine curvature. Segments in some embodiments have a curvilinear delta cross sectional shape and/or have crosshatched grooves in exposed surfaces. Many of the embodiments are useful in transforaminal lumbar interbody fusion (TLIF).

64 Claims, 11 Drawing Sheets

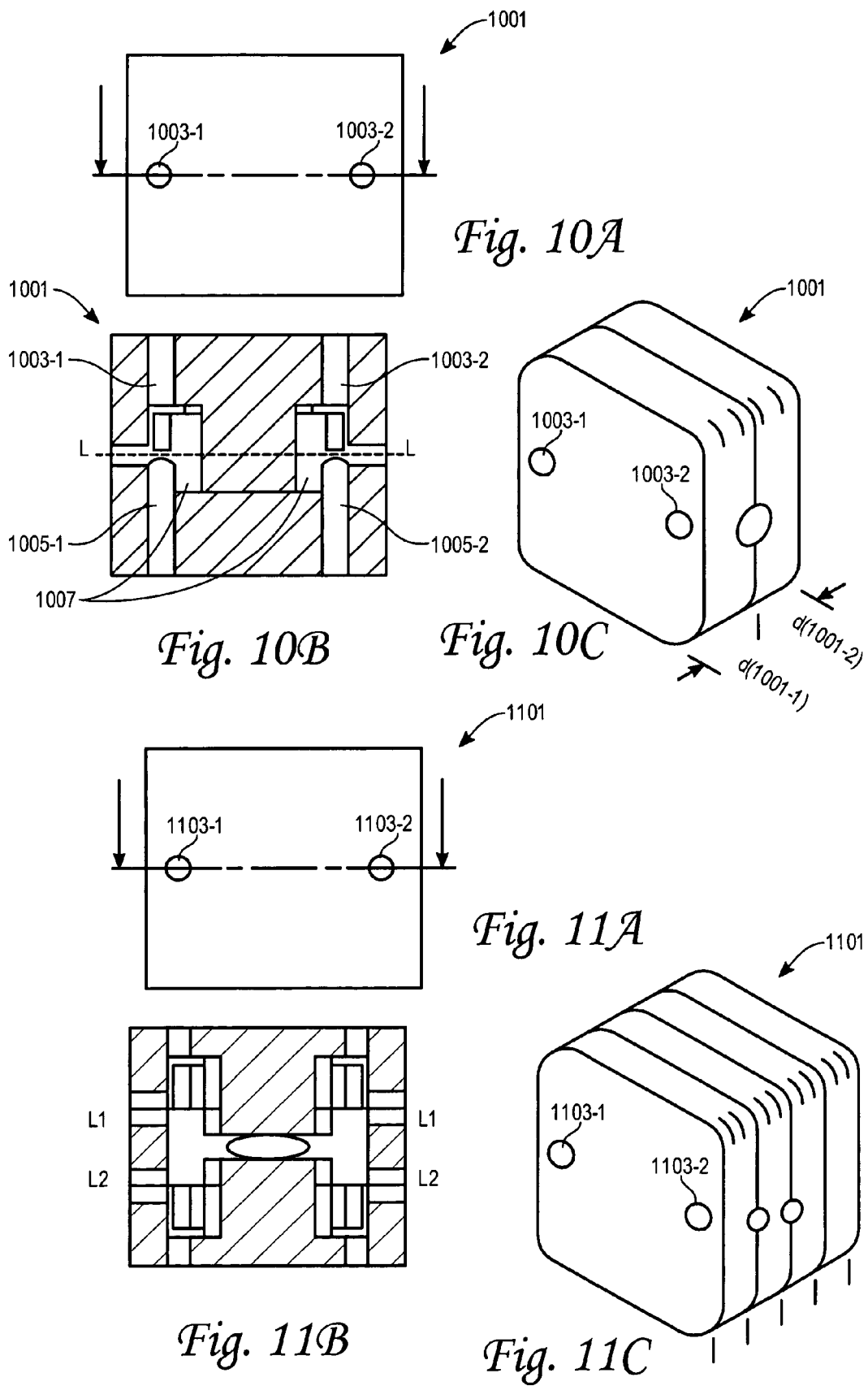

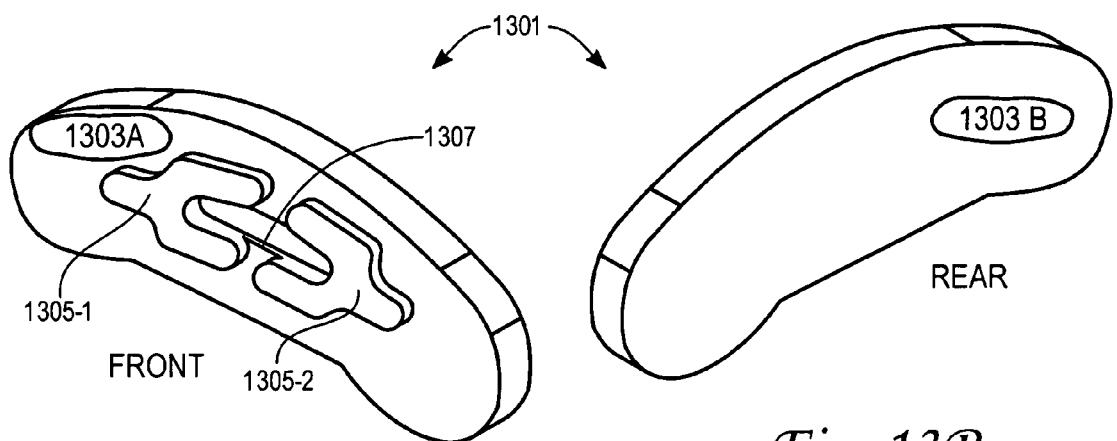
Fig. 13A
Fig. 13B
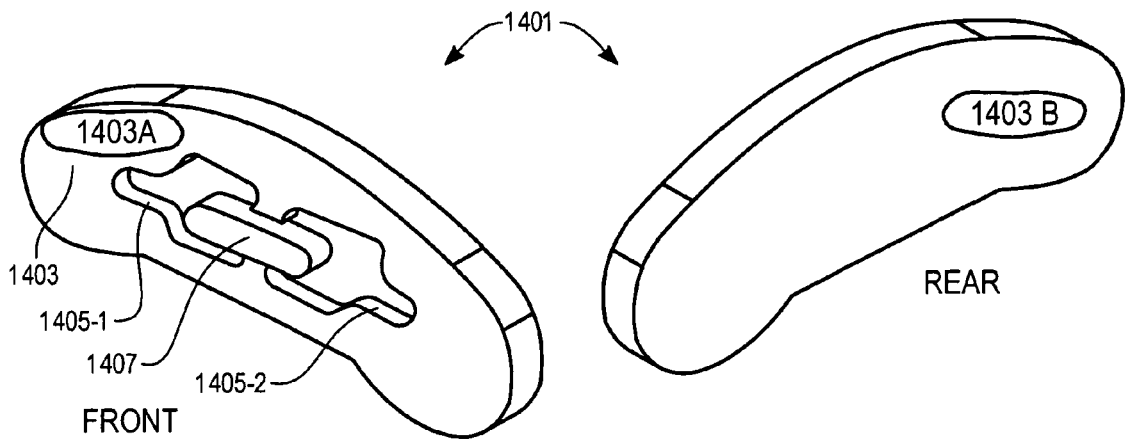
Fig. 14A
Fig. 14B

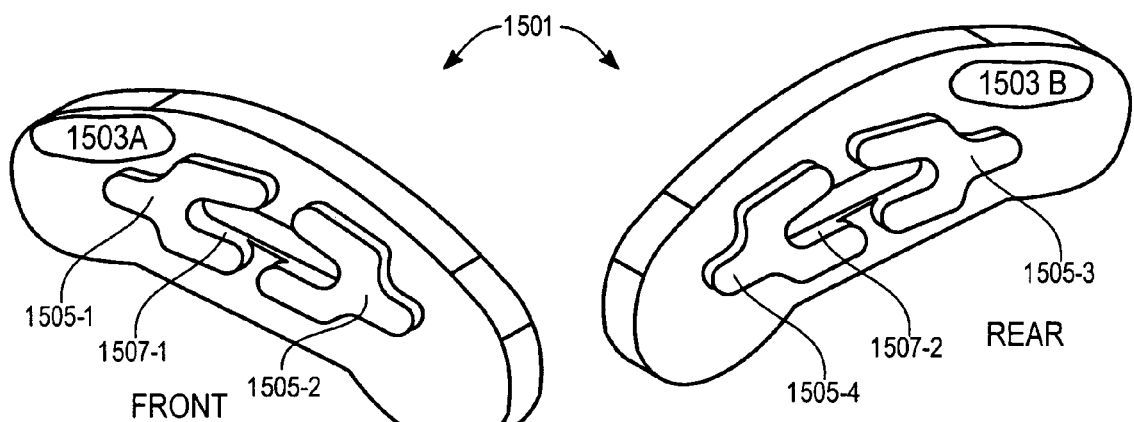
Fig. 15A
Fig. 15B
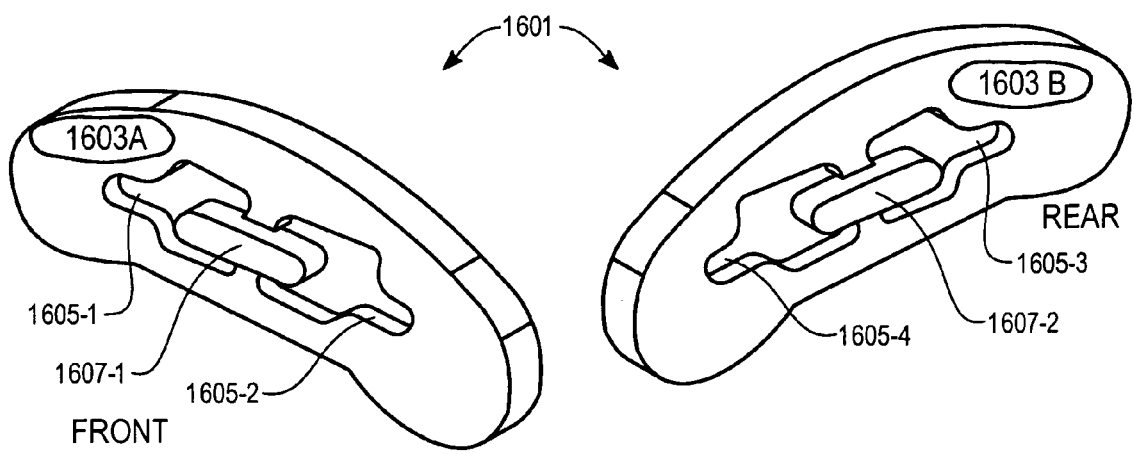
Fig. 16A
Fig. 16B

BONE IMPLANT WITH OSTEO-INDUCING STRUCTURE

FIELD OF THE INVENTION

This invention relates to inter-body spinal fusion bone grafts with multiple segments, and more particularly a transforaminal lumbar interbody fusion implant.

BACKGROUND OF THE INVENTION

A spine of a vertebrate animal, including a human, has a space between adjacent vertebrae, referred to as the "interbody space" of the spine. This space is occupied by a disk including an annulus of firm material, surrounding a moist, mushy central material that is called the nucleus. This space separates and cushions adjacent vertebrae. Medical conditions of degenerative disk disease that cause severe back pain include herniated nucleus pulposis and collapse disk space that cause compression of spinal cord roots. Intervertebral spinal fusion is a surgical technique that often relieves back pain arising from these medical conditions, by removing an affected disk, fusing two adjacent vertebral bodies together and by inserting one or more implants that allow bone to grow between the two fused intervertebal bodies where a disk has been removed. In the field of prosthetic implants, the materials used include bone grafts (autografts, allografts and xenografts) and implants produced by non-bone materials, such as stainless steel, titanium, ceramics and plastics. Success or failure of a bone graft or non-bone implant depends in part on whether the insert remains at the implant location, whether the implant is cellularized to induce new bone formation, and whether the insert can withstand the resulting mechanical load and remain stable. Inter-body fusion between two adjacent vertebral bodies in a space occupied by a disk is recognized and encouraged for good biomechanical, neurophysiological and anatomical practices.

Lumbar interbody fusion is performed from an anterior or posterior location, although transversely oriented positions are used as well. In posterior lumbar interbody fusion (PLIF), surgeons have traditionally used an open approach to perform a spinal fusion procedure. This involves making an incision along a center line on the back, stripping bands of back muscles from the spine, and pulling or retracting the muscles to each side of the opening so that the spine and vertebra can be viewed and accessed for device implantation. The main benefit of a PLIF procedure is the degree of exposure and accessibility provided for the surgeon. However, several studies have shown that extensive surgical exposure for extended time periods (hours) can seriously injure or degrade the major back muscles and can cause post-surgical pain. Also, two implant spacers usually need to be surgically inserted from two posterior portals.

Transforaminal lumbar interbody fusion (TLIF) is an improvement of the PLIF procedure in which the bone spacer is inserted from a unilateral approach posteriolaterally, without having to forcefully retract the nerve roots. TLIF minimizes the amount of surgical dissection required to access the intervertebral space and preserves more of the posterior elements. In a TLIF procedure, several traditional PLIF implant devices, such as threaded titanium or stainless steel cages, allograft wedges and rings have been used, with mixed results. However, these devices are not easily inserted into the affected disk space and may produce temporary or permanent nerve damage. Use of a threaded titanium or stainless steel nerve cage requires drilling and cutting into vertebral endplates.

U.S. Pat. No. 5,769,897, issued to Harle, discloses improvements in artificial bone material, such as bio-ceramics, that can be used to form segments of or entire artificial bones for implantation. According to the '897 patent, synthetic bone has two components: (1) a first component to sustain the required mechanical strength and (2) a second component to enhance bio-integration with natural bone tissue. As illustrated in FIG. 1A, the first component has at least one accessible void.

U.S. Pat. No. 5,888,227, issued to Cottle, discloses an inter-vertebral implant having a frame-line cage that encloses a cavity and has perforated cover and face bases as bone contacting surfaces, illustrated herein in FIG. 1B. These background references indicate the significance of osteo-induction for new bone formation after implantation but require inclusion of an artificial substance (metal, bio-ceramic, etc.) to provide the required mechanical strength and stability. However, an implant system based on natural bone substances may not withstand the estimated 500-1500 Newtons/$cm^2$ pressure to which portions of a spine are subjected.

U.S. Pat. No. 6,458,158, issued to Anderson et al, discloses a composite bone graft, including a cancellous (porous) bone located between two cortical bones, with one or more cortical bone pins to hold a three-piece structure together, as illustrated in FIG. 1C. The cancellous bone is positioned to promote osteo-inductions for bone growth. One problem with provision of a plurality of perforation channels is that these channels may reduce mechanical strength of the resulting structure.

U.S. Patent Application US2002/0029084, filed by Paul, discloses a bone fusion implant for repair or replacement of bone and including at least two bone fragments (male and female), joined together by an interlocking arrangement, as illustrated in FIG. 1D. This approach appears to provide the required mechanical strength but does not appear to encourage osteo-induction at the interface of the bone fragments; the bone fragments remain separate, with little or no prospect of fusion.

What is needed is a bone implant system that uses single or multiple segments without use of bone pins, that accommodates multiple perforation channels and voids to promote autograft, allograft and/or xenograft osteo-induction, without loss of the required mechanical strength and stability. A need also exists for an improved transforaminal lumbar interbody fusion (TLIF) implant system that allows adequate host-graft interface with multiple segments of a bone implant system, and which accommodates perforations and voids to promote osteo-induction.

SUMMARY OF THE INVENTION

These needs are met by the invention, which provides multiple bone graft segments to allow matching of different interverbral separations, provides a plurality of voids and perforation channels to promote osteo-induction, and manifests mechanical strength sufficient to withstand the maximum likely compression stress that a portion of a spine may experience. The multiple bone segments interlock together, and no bone pins are required. The voids and perforation channels serve as centers for bone induction, and the bone graft promotes growth and fusion of patient bone at and adjacent to the bone implant location, by promoting osteo-induction. The system is stable against very high stress compression, extrusion and rotation of one or more bone implant segments. Optionally, each segment has at least one perforation channels and/or a void that communicates with a perforation channel and/or a void of one or more adjacent segments, to promote osteo-induction.

The invention is an intervertebral implant system using autograft, allograft or xenograft components for transforaminal lumbar interbody fusion (TLIF) surgery. In a preferred embodiment, the TLIF procedure uses one or more curvilinear delta shaped implant segments, with curved features at corners of the device. Use of a rounded delta shape provides a TLIF implant with anatomically safe insertion during surgery. The superior and inferior segments that fuse on the vertebral end plates are complementary and have appropriate concave, convex and chamfer features. Concave and convex features are selected to closely match anatomical shapes of the vertebral end plates. Inclusion of a chamfer feature ensures safe insertion of the device into the affected disk space. Surfaces for the superior and inferior segments have a small, positive lordosis angle (e.g., about 1-8°, preferably about 5°) for recovery of lumbar lordosis curvature.

The bone graft system preferably includes two or more implant segments that join or interlock together without requiring use of bone pins or similar attachment components. Sizeable voids and/or perforation channels are provided near a center of a bone graft. These voids receive the perforation channels and serve as centers for bone induction, and the bone graft promotes bone growth and fusion at the implant location, through promotion of osteo-induction. This action provides stability against compression, shifting (translation) and rotation after implantation. Interlocking of segments occurs through provision of complementary male and female shapes with improved interference fit of the complementary shapes. Optional chamfered surfaces facilitate fabrication and placement of a segment.

BRIEF DESCRIPTION OF THE DRAWINGS

FIGS. 10A-10C illustrate a two-segment embodiment with voids and perforation channels.

FIGS. 11A-11C illustrate a four-segment embodiment with voids and perforation channels.

FIGS. 13A-13B, 14A-14B, 15A-15B, 16A-16B and 17A-17B illustrate other embodiments of spinal implant segments.

DESCRIPTION OF BEST MODES OF THE INVENTION

Figure 1A:
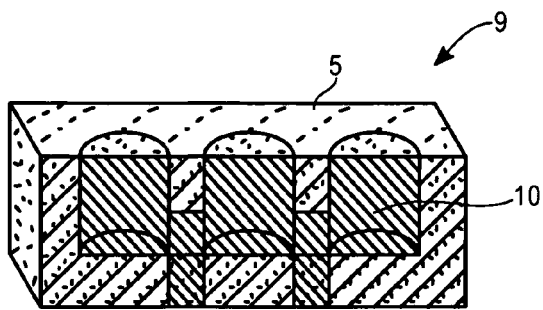
FIGS. 1A-1D illustrate some bone implant configurations from the prior art.
Figure 1B:
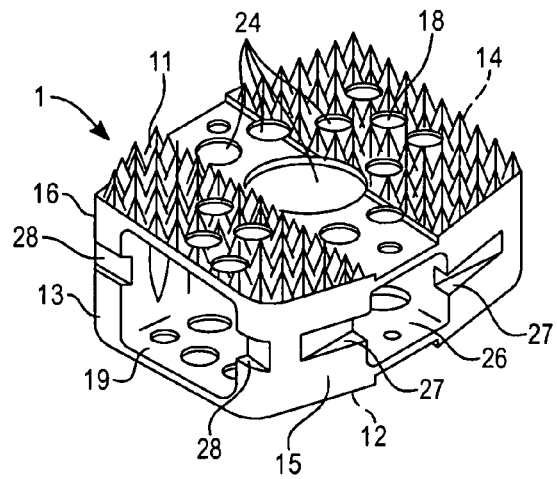
Figure 1C:
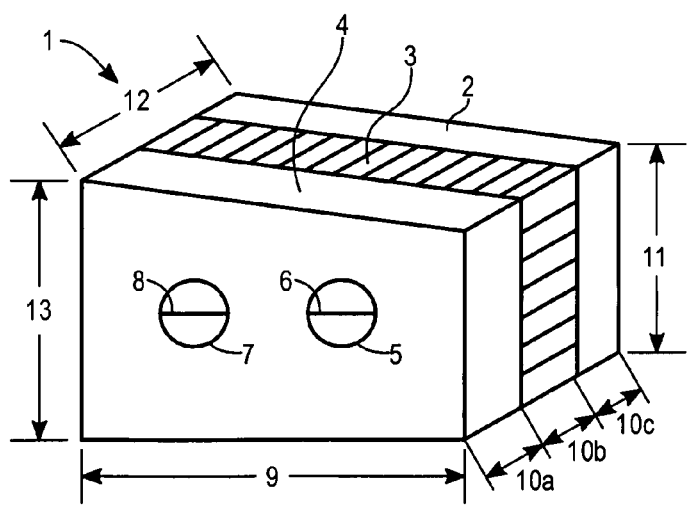
Figure 1D:
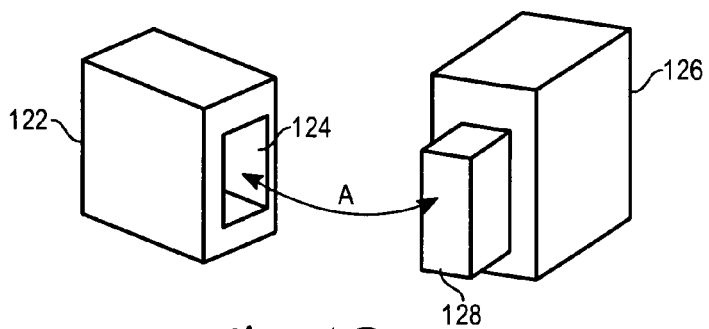
Figure 2A:
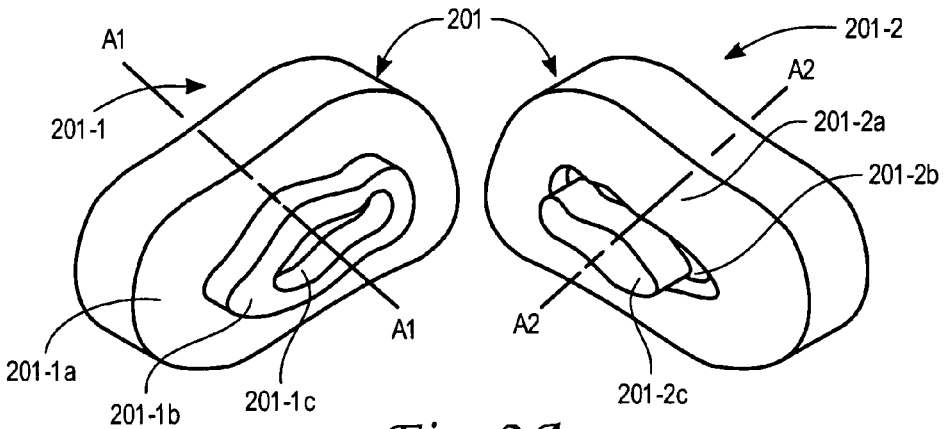
FIGS. 2A-2E illustrates one embodiment of the invention, using interlocking male/female segments to provide location stability and strength.
Figure 2B:
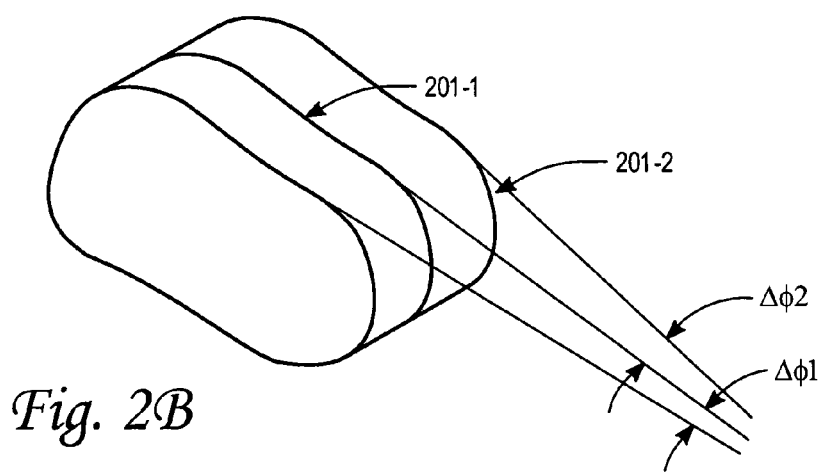

FIG. 2A illustrates two segments, 201-1 and 201-2, having respective axes A1-A1 and A2-A2, according to one embodiment of the invention, which can be coupled or fitted together along a common axis to form an interlocking bone graft implant system, as illustrated in FIG. 2B. The bone implant segment 201-1 includes a first female annular region 201-1a, surrounding a second male annular region 201-1b, which in turn surrounds a third female annular region 201-1c. These annular regions may be, but need not be, cylindrically symmetric. The bone implant segment 201-2 includes a first male annular region 201-2a, surrounding a second female annular region 201-2b, which in turn surrounds a third male annular region 201-2c. Preferably, the material used here is predominantly cortical bone, although cancellous bone and other natural bone substances can also be used.

The implant segments 201-1 and 201-2 fit together so that the first female annular region 201-1a receives the first male annular region 201-2a, the second male annular region 201-1b is received by the second female annular region 201-2b, and the third female annular region 201-1c receives the third male annular region 201-2c, as indicated in FIG. 2A. As a result of this coupling, the first and second implant segments, 201-1 and 201-2, fit together to form an integrated bone implant system, shown in FIG. 2B. Normally, two planes (transverse to the segment axis) that define the extent of the segment in the axial direction will be substantially parallel to each other. However, because of the natural curvature of the spine, especially in the cervical region, it may be preferable to provide a small non-negative angle $\Delta\phi1$ and/or $\Delta\phi2$ (e.g., 0°-8°), between the two transverse planes for the first segment 201-1 and/or for the second segment 202-2, which closely approximates the natural curvature for the corresponding intervertebral separation distance, as illustrated in FIG. 2B.

Figure 2C:
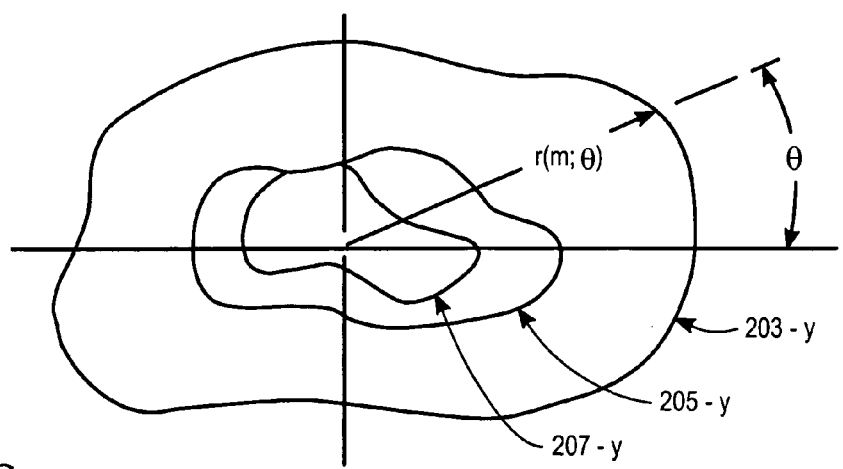

As noted in the preceding, the annular regions 201-1x and 201-2x (x=a, b, c) need not be cylindrically symmetric. FIG. 2C is a top view of a bone implant segment 202, in which each annular region boundary, 203-y, 205-y and 207-y (y=1, 2), is defined by an arbitrary closed curve, with the local radius r=r(m;θ) (m=203-y, 205-y, 207-y) being specified in terms of a polar angle θ (θ≦θ<2π) that is measured in a plane where two segments (e.g., 201-1 and 201-2) fit together. The local radius r=r(m;θ) must define a closed curve so that r(m;θ+2π)= r(m;θ); but the curve thus defined is otherwise arbitrary and may be convex or non-convex, monotonic or non-monotonic, and may have a constant or non-constant radius. Optionally, a portion of the curve given by r=r(m=203-y;θ) may coincide with a portion of the curve given by r=r(m=205-y;θ); and/or a portion of the curve given by r=r(m=205-y;θ) may coincide with a portion of the curve given by r=r(m=207-y;θ), as illustrated in FIG. 2C. The third male annular region 201-2c and the corresponding third female annular region 201-1c have matching outer boundaries (207-y) with a small offset so that these two annular regions can be fitted together with a selected amount of friction. Similarly, the second male annular region 201-1b and the corresponding second female annular region 201-2b have matching inner boundaries (207-y) and matching outer boundaries (205-y) with a small offset (e.g., 0.03-0.08 mm); and the first male annular region 201-2a and the corresponding second female annular region 201-1a have matching inner boundaries (205-y) and matching outer boundaries (203-y) with a small offset.

Figure 2D:
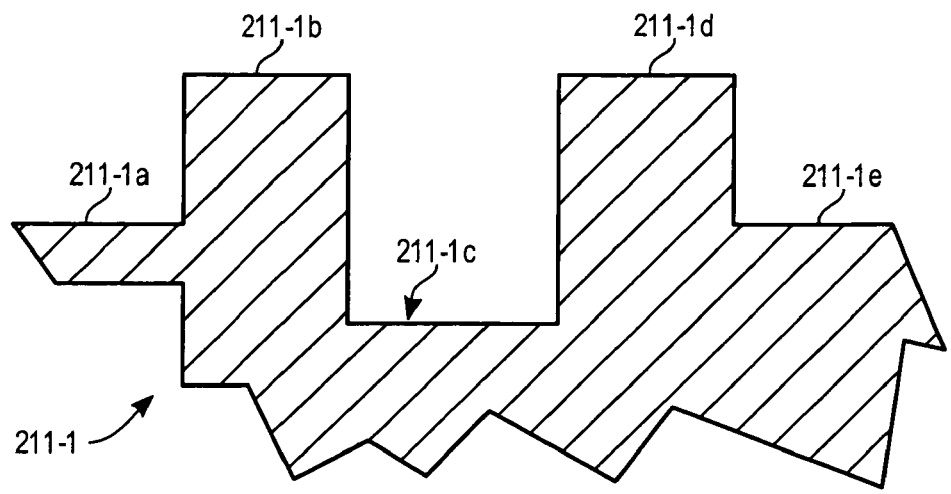
Figure 2E:
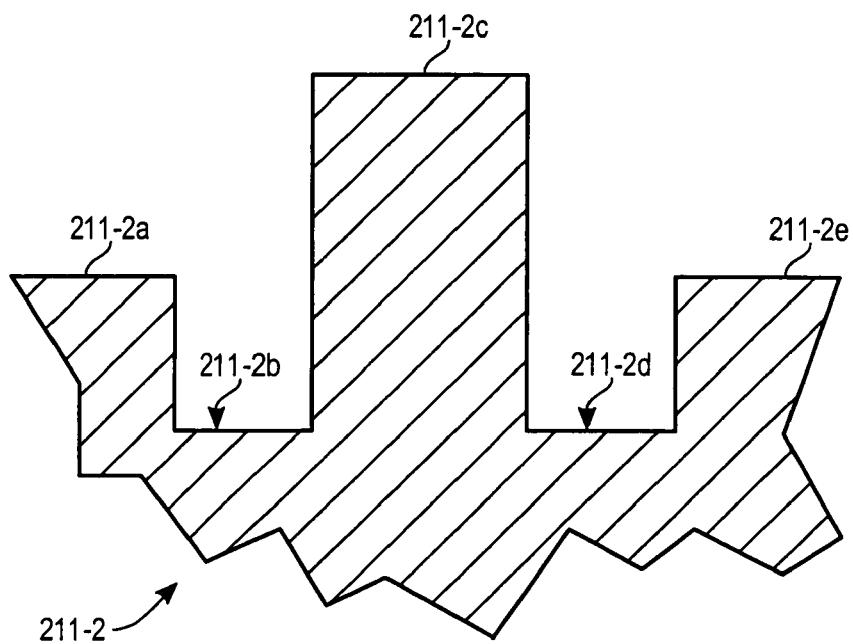
Figure 3A:
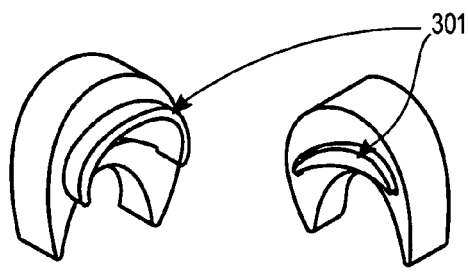
FIGS. 3A-3B illustrate an embodiment of the invention with N=2 annular regions.
Figure 3B:
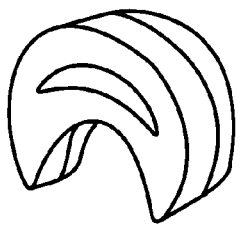

FIGS. 2D and 2E are cross sectional views of an alternative embodiment having five annular regions, 211-2a, 211-1b, 211-2c, 211-1d and 211-2e, having "male extensions" (extending outward and oriented approximately parallel to an axis AA of the corresponding segment 211-1 or 211-2) that fit together with five annular regions, 211-1a, 211-2b, 211-1c, 211-2d and 211-1e, having "female extensions" (extending inward and oriented approximately parallel to the axis AA), respectively. The number of male annular regions, or the number of female annular regions, may be any number N at least equal to 2, but N≧3 is preferred for enhanced stability. FIGS. 3A and 3B illustrate a configuration with N=2 annular regions.

Figure 4A:
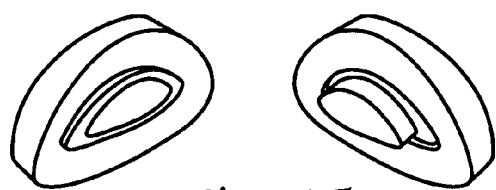
FIGS. 4A-4B, 5A-5B and 6A-6B illustrate embodiments of the invention with N=3 annular regions.
Figure 5A:
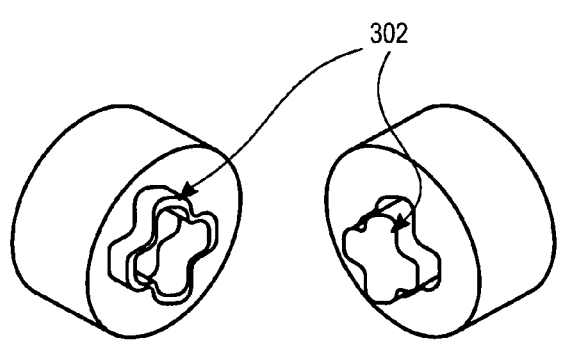
Figure 4B:
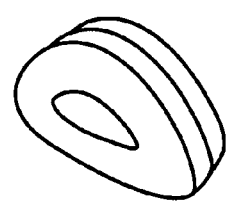
Figure 5B:
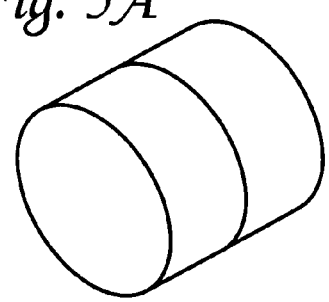
Figure 6A:
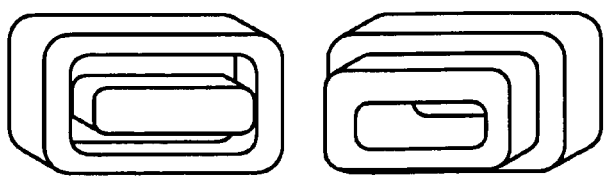
Figure 6B:
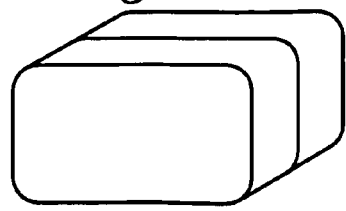

FIGS. 4A and 4B illustrate a configuration with N=3 annular regions with boundaries that are shaped as ovals. FIGS. 5A and 5B illustrate a configuration with N=3 annular regions with boundaries that are shaped as four-sided clover leafs. FIGS. 6A and 6B illustrate a configuration with N=3 annular regions with boundaries that are shaped as rectangles (or more generally as regular or non-regular polygons).

Figure 7A:
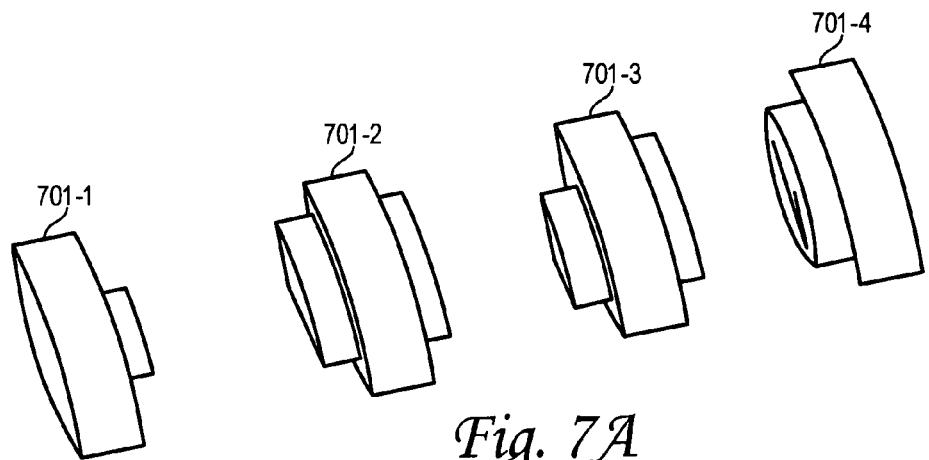
FIG. 7 illustrates interlocking of K=4 axial segments together to provide a selected intervertebral separation distance.
Figure 7B:
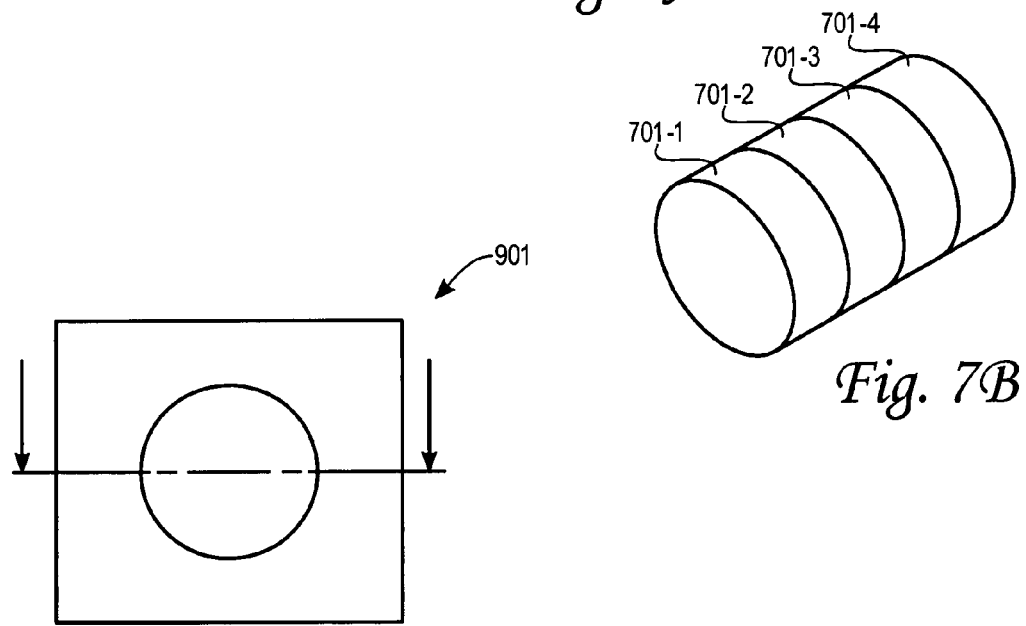

FIGS. 7A and 7B illustrate a fitting together of K=4 segments, 701-$k$ ($k$=1, 2, 3, 4) to form an integrated bone implant system, with corresponding axial thicknesses d=$d_k$ ($k$=1, 2, 3, 4). The interior segments, 701-2 and 701-3, may have the same axial thickness ($d_2$=$d_3$) or, preferably, may have different axial thicknesses ($d_2 \neq d_3$), as discussed in the following. Preferably, the number K of segments in an integrated bone implant system is at least 2.

Figure 8A:
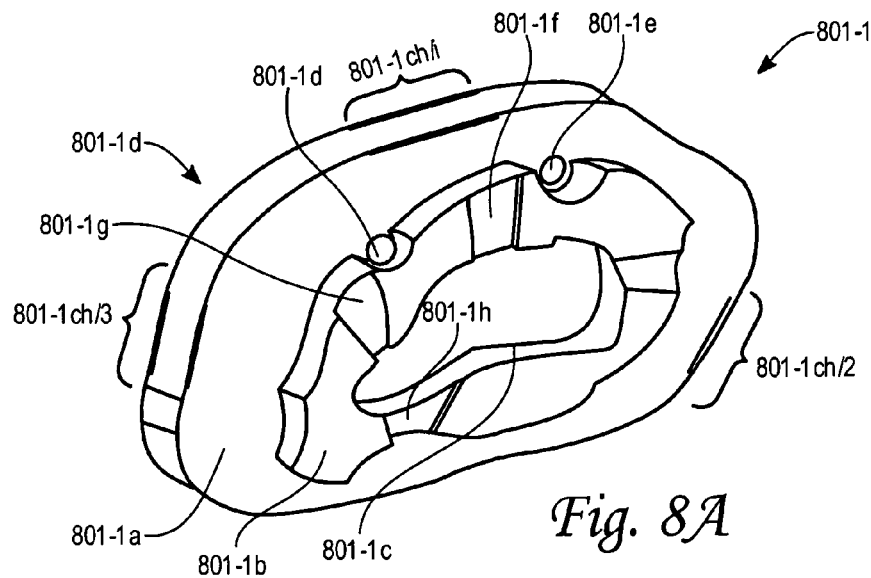
FIGS. 8A-8C illustrate provision of voids and perforation channels in a male-female interlocking pair of segments.

FIG. 8A illustrates two segments, 801-1 and 801-2, having corresponding male and female interlocking annular regions and being provided with voids and perforation channels to promote osteo-induction. The first segment 801-1 includes a first female annular (outer) region 801-1$a$; a second male annular (middle) region 801-1$b$; a third female annular (inner) region 801-1$c$; one or more perforation channels, 801-1$d$ and 801-1$e$, each extending from an exposed surface of the first segment to an interior location within the segment; and one or more voids, 801-1$f$, 801-1$g$ and 801-1$h$ within the interior of the first segment, where no material is present from the first segment and no material is present from the second segment.

The second segment 801-2 includes a first male annular (outer) region 801-2$a$; a second female annular (middle) region 801-2$b$; a third male annular (inner) region 801-2$c$; one or more perforation channels, 801-2$d$ and 801-2$e$ that extend from an exposed surface of the second segment to the interior; and one or more voids, 801-2$f$ and 801-2$g$, within the interior of the second segment. Optionally, a perforation channel from each of the first segment 801-1 and second segment 801-2, such as 801-1$e$ and 801-2$d$, respectively, can be aligned with each other to provide a perforation channel that extends from an exposed surface of the first segment to an exposed surface of the second segment, to promote natural bone growth to bind the first and second segments together.

Figure 8B:
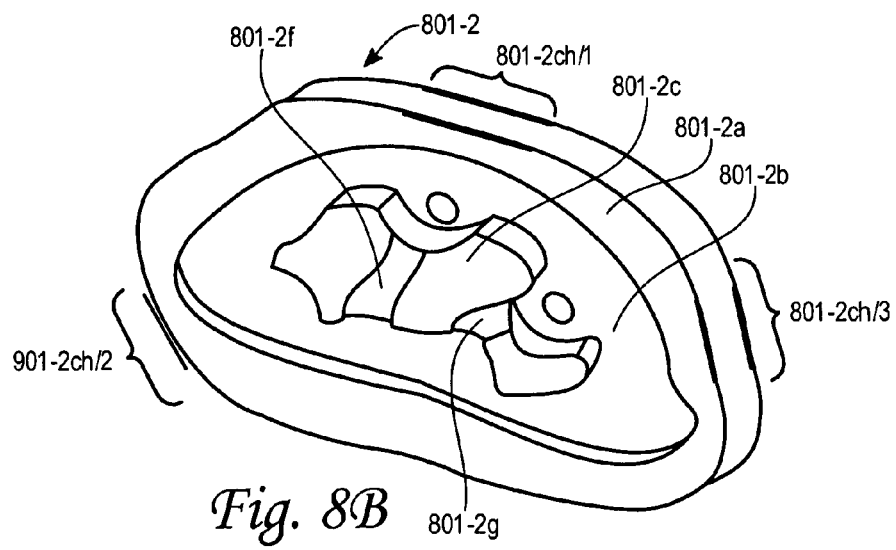
Figure 8C:
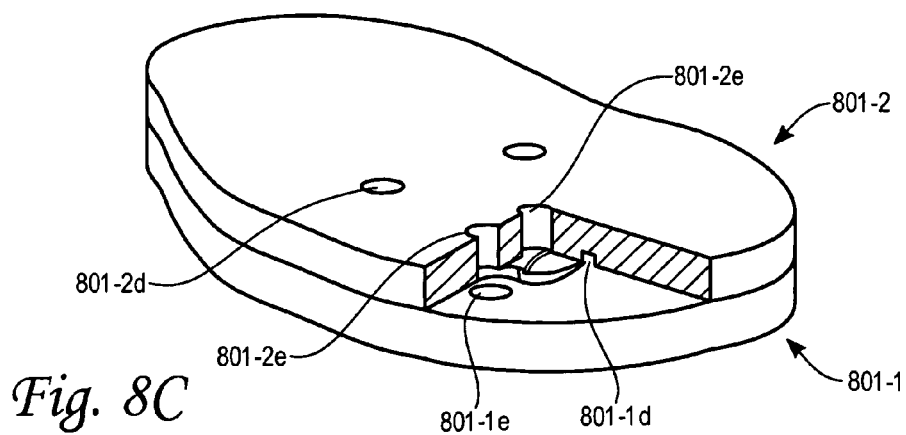

FIG. 8B is a cutaway view showing the first and second segments, 801-1 and 801-2, interlocked with each other so that: the first female annular region 801-1$a$ and the first male annular region 801-2$a$ mate with each other; the second male annular region 801-1$b$ and the second female annular region 801-2$b$ mate with each other; and the third female annular region 801-1$c$ and the third male annular region 801-2$c$ mate with each other, apart from the perforation channels and voids discussed in the preceding paragraph.

Optionally, two or more (preferably three or more) chamfered surfaces are provided on each segment of any implant device to allow easier fabrication and/or easier positioning and installation of the segment. On the first segment 801-1 in FIG. 8A, the spaced apart portions, 801-1$ch$/1, 801-1$ch$/2 and 801-1$ch$/3, of the exposed circumferential surface are chamfered or flattened to allow easier fabrication and/or positioning of the first segment. Preferably, no two planes corresponding to the three portions, 801-1$ch$/1, 801-1$ch$/2 and 801-1$ch$/3, of the circumferential surface of the first segment 801-1 are parallel so that the normal vectors for these three portions are independent. Three spaced apart portions, 801-2$ch$/1, 801-2$ch$/2 and 801-2$ch$/3, of the second segment 801-2 in FIG. 8A are similarly arranged. Optionally, but not necessarily, the plane of each chamfered portion, 801-1$ch$/1, 801-1$ch$/2 and 801-1$ch$/3, of the first segment 801-1, may be parallel to, or coincident with, a plane of a corresponding chamfered portion, 801-2$ch$/1, 801-2$ch$/2 and 801-2$ch$/3, of the second segment, when the first and second segments are assembled and interlocked.

The number of chamfered portions of a surface of a segment may be reduced to two opposed portions that are approximately parallel to each other, to provide two opposed gripping surfaces for fabrication and/or positioning of a segment. However, provision of three or more chamfered portions with at least three non-parallel planes is preferred, for improved stability and firmness of grip.

Figure 9A:
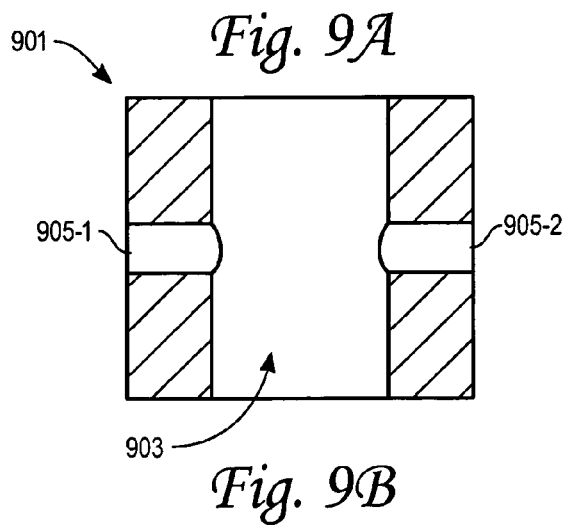
FIGS. 9A-9C illustrate a single segment embodiment with voids and perforation channels.
Figure 9B:
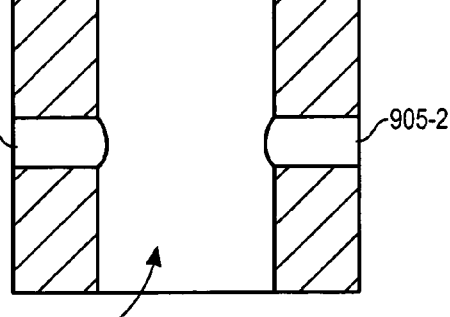
Figure 9C:
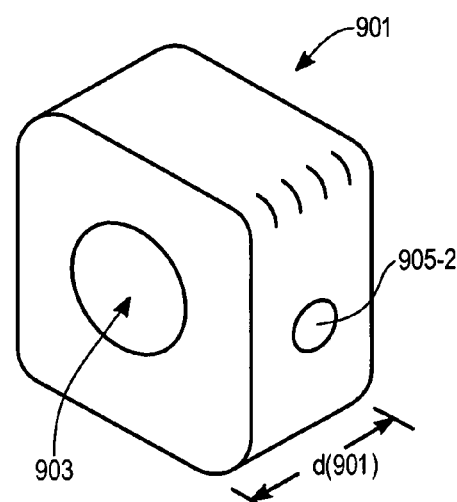

FIGS. 9A, 9B and 9C are a top view, cross sectional side view and perspective view, respectively, of a single segment configuration 901 having a first axially oriented aperture 903 and J transversely oriented apertures 905-$j$ ($j$=1, 2, 3, ..., J; J≧1). The axially oriented aperture 903 and the transversely oriented apertures 905-$j$ provide voids and channels to encourage osteo-induction or bone growth within these apertures. The axial length d(901) of the single segment bone implant system 901 is chosen to correspond to the intervertebral separation distance on the spine.

FIGS. 10A, 10B, and 10C are a top view, cross sectional side view and perspective view, respectively, of a two-segment configuration 1001 (K=2). The heavy line LL in the cross sectional view (FIG. 10B) indicates where a first segment 1001-1 and a second segment 1001-2 make contact and fit together. The first segment 1001-1 has one or more axially oriented apertures 1003-$h1$ ($h1$=1, ..., H1; H1≧1), preferably spaced apart from a center line within the first segment. The second segment 1001-2 has one or more axially oriented apertures 1005-$h2$ ($h2$=1, ..., H2; H2≧1), preferably spaced apart from a center line within the second segment. The first segment 1001 also has one or more axially oriented apertures 1007 that may be offset from, or may include, the center line within the first segment. The axial lengths d(1001-1) and d(1001-2) of the two segments may have any convenient values.

In one embodiment, the first and second segments, 1001-1 and 1001-2, have approximately cylindrically symmetric solid center components, 1009-1 and 1009-2, respectively, that preferably contact each other axially along a portion of the contact line LL, as shown. The regions of contact of the first and second segments, 1001-1 and 1001-2, along the contact line LL must carry the mechanical load (normally a compressive load) exerted on the bone implant system 1001.

Cortical bone has measured ranges of ultimate stress of 1.56-2.12, 1.07-1.46, and 0.73-0.82 (in units of $10^4$ Newtons/cm$^2$) for compression, tension and shear, respectively. Cancellous bone has measured ranges of 0.015-0.5, 0.03-0.2 and 0.066 (in units of $10^4$ Newtons/cm$^2$) for compression, tension and shear, respectively.

A cylindrical ring of cortical bone, having inner and outer radii of r1 and r2 (in cm), respectively, will have a compressive strength (before mechanical breakdown) in the range of (4.90-6.66)(r2$^2$-r1$^2$)×$10^4$ (Newtons). The area of this annulus should be at least about 0.01 cm$^2$ in order to be mechanically stable under a compressive load of up to 500 Newtons.

FIGS. 11A, 11B and 11C are a top view, cross sectional side view and perspective view, respectively, of a three-segment configuration 1101 (K=3), including the segments 1101-1, 1101-2 and 1101-3. The heavy line L1-L1 indicates where the segments 1101-1 and 1101-2 make contact and fit together. The heavy line L2-L2 indicates where the segments 1101-2 and 1101-3 make contact and fit together. The effective axial lengths of the three segments are d(1101-1), d(1101-2) and d(1101-3) and are chosen so that the sum of these effective axial lengths is substantially or approximately equal to the desired intervertebral separation distance, which is often between 5 mm and 20 mm. The external segment axial lengths, d(1101-1) and d(1101-3), are preferably each chosen to be no more than 2.5-4 mm so that an interior segment axial length, such as d(1101-2), can be at least 1-2 mm for adequate mechanical strength and stability.

Where K≧4 segments are provided, in an embodiment similar to the one shown in FIGS. 11A-11C, the K-2 interior segment(s) may have substantially the same cross sectional shapes and may have substantially the same axial lengths.

The male-female interlocking relationship between adjacent segments enhances the mechanical strength and stability and allows two adjacent, interlocked segments to resist translation and/or rotation relative to each other. Provision of a perforation channel or a void that communicates with each of two or more adjacent segments may allow natural bone to grow into the channel, perforation or void and to strengthen the grip of the adjacent segments on each other. No bone pins are required here.

The cross sectional shapes of the segments shown in FIGS. 2A through 8B are generally ovular. Another suitable cross sectional shape for TLIF applications is a curvilinear delta shape, shown in one embodiment in FIGS. 12A, 12B and 12C, wherein portions of an originally triangular cross sectional shape are trimmed away adjacent to one or more corners or apices to provide one or more rounded corners or apices. The curvilinear delta shape of the implant device 1201, shown perspectively in FIG. 12A in a plane defined by a sagital direction and a coronal direction, and in a top view in FIG. 12B, provides enhanced mechanical stability in the sagital and coronal planes.

Figure 12A:
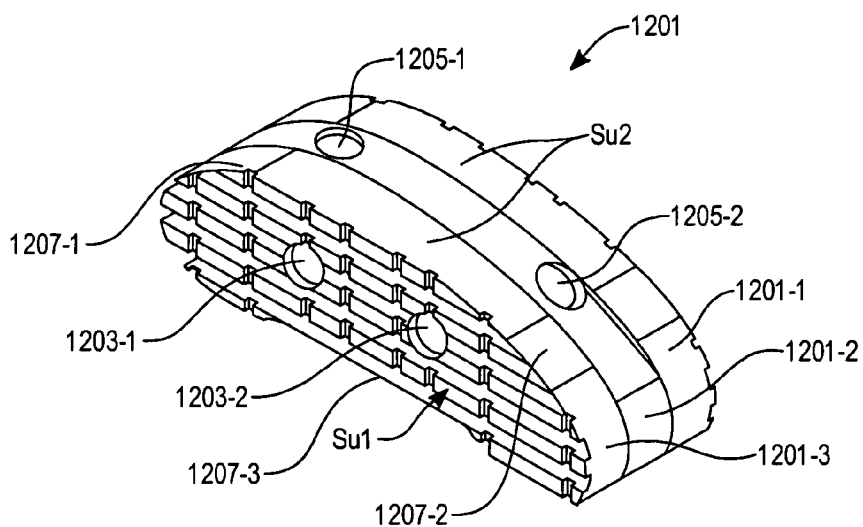
FIGS. 12A-12D illustrate a three-segment osteo-inductive structure with a curvilinear delta cross sectional shape and (optional) grooves.
Figure 12B:
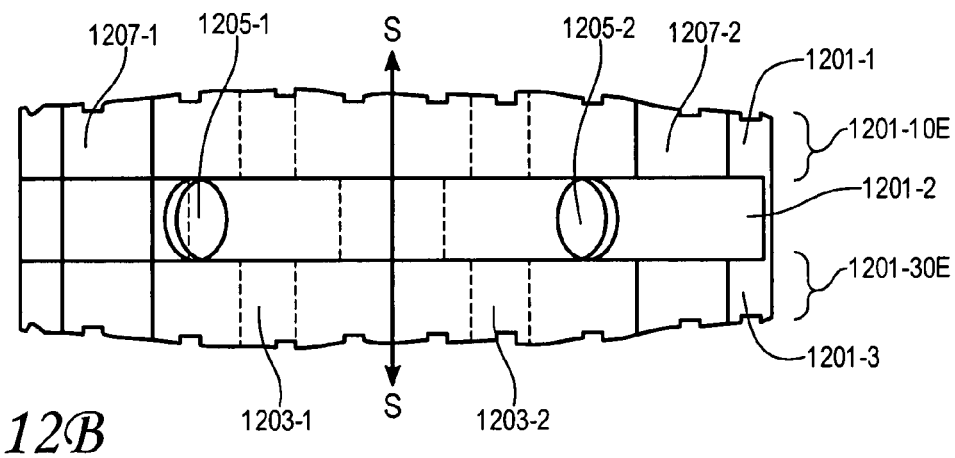
Figure 12C:
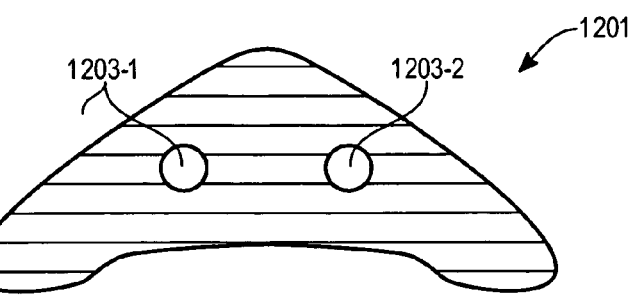

FIG. 12A indicates a crosshatched (e.g., longitudinal and/ or lateral) groove pattern (e.g., as made by a saw or other cutting instrument), optionally made in a surface Su of the bone, in order to provide better surface compliance with another surface that is contacted by the surface Su1. The presence of the grooves allows the surface S, shown in cross section in FIG. 12B, to bend to approximate a shape of a surface against which the surface Su1 is positioned. The grooves may be provided in one direction (lateral or longitudinal) or in both directions, and the alignment of the two sets of grooves need not be perpendicular.

The implant device 1201 shown in FIGS. 12A, 12B, 12C and 12D includes at least three contiguous segments, 1201-1, 1201-2 and 1201-3, having one or more apertures, channels or voids, 1203-1 and 1203-2, that each have a common alignment parallel to a longitudinal (spine) axis SS. Optionally, an interior segment, for example, 1203-2, also has one or more laterally oriented apertures, channels or voids, 1205-1 and 1205-2. Each of the apertures, 1203-1, 1203-2, 1205-1 and 1205-2, provides a void region for growth of bone therein. Optionally, three or more spaced apart chamfered (planar) surfaces, 1207-1, 1207-2 and 1207-3 are included in each of one or more of the segments, 1261-1 and 1201-2, for aid in alignment in manufacturing and/or positioning of the device 1201. Preferably, the outer radial ends, 1201-10E and or 1201-30E are tapered, having a small positive angle (e.g., 1°-5°) between planes, 1209-1 and 1209-2, of two exposed surfaces of the device 1201. The segments 1201-1, 1201-2 and 1201-3 may be interconnected via male-female interlocking relationships as described herein. The outer radial ends, 1201-10E and 1201-30E, have a reduced physical extent, shown in FIG. 12D, in a direction normal to the spine axis SS, to provide easier lateral insertion of the spinal implant and to provide improved mechanical stability in the coronal plane in a TLIF operation, in which the spine implant device 1201 is inserted into the spine from a side of the patient.

Figure 12D:
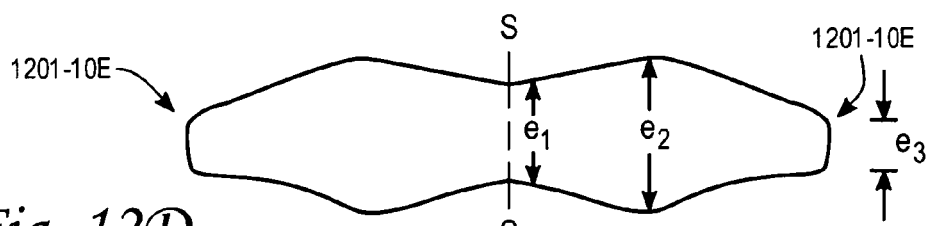

Optionally, as shown in FIG. 12D, the physical extent of the spinal implant in the direction of the spine axis SS may increase monotonically from a first value e1 at the center (coincident with the spine axis) to a second value e2 (>e1) at an intermediate radius and then decrease montonically to a third value e3 (<e2) at a maximum radius of the spinal implant.

FIGS. 13A and 13B are front and rear views of a segment 1301, illustrating a profile of another segment according to the invention. The segment 1301 includes a first substantially planar (front) surface 1303A having two or more male extensions, 1305-1 and 1305-2, that extend outward from a first (front) planar surface of the segment; and a second substantially planar (rear) surface 1303B that has no male or female extensions thereon. The first surface 1303A also has a female extension 1307, defined relative to the first surface 1303A, that extends inward from the first surface and is partly surrounded by the male extensions 1305-1 and 1305-2, as shown.

FIGS. 14A and 14B are front and rear views of a segment 1401, illustrating a profile of another segment according to the invention. The segment 1401 includes a first substantially planar (front) surface 1403A having two or more female extensions, 1405-1 and 1405-2, that extend inward from a first (front) planar surface of the segment; and a second substantially planar (rear) surface 1403B that has no male or female extensions thereon. The first surface 1403A also has a male extension 1407 that extends outward from the first surface 1403 and is partly surrounded by the male extensions 1405-1 and 1405-2, as shown.

Optionally, the first surfaces, 1303A and 1403A, of the segments 1301 and 1401 "mate" or fit together so that the male extension 1407 is received by the female extension 1307, and the male extensions, 1305-1 and 1305-2, are received by the female extensions, 1405-1 and 1405-2, thereby substantially locking the segments 1301 and 1401 together. In the combined version shown in FIGS. 13A, 13B, 14A and 14B, the second surfaces, 1303B and 1403B, of the have no male or female extensions features thereon.

In another version, illustrated in FIGS. 15A and 15B, a first segment 1501 has first and second planar surfaces, 1503A and 1503B. The first planar surface 1503A of the segment 1501 has first and second spaced apart male extensions, 1505-1 and 1505-2, partly surrounding a female extension 1507-1 that optionally extends from the first surface 1503A to the second surface 1503B. The second planar surface 1503B has third and fourth spaced apart male extensions, 1505-3 and 1505-4, partly surrounding a female extension 1507-2 that optionally extends from the second surface 1503B to the first surface 1503A so that 1507-1 is identical with 1507-2. Alternatively, none of the female extensions, 1507-1 and 1507-2 extends through the segment 1501.

In a companion segment 1601, shown in FIGS. 16A and 16B, a first planar surface 1603A of the segment 1601 has first and second spaced apart female extensions, 1605-1 and 1605-2, partly surrounding a male extension 1607-1. A second planar surface 1603B has third and fourth spaced apart female extensions, 1605-3 and 1605-4, partly surrounding a male extension 1607-2. The first surface 1503A (or second surface 1503B) of the segment 1501 and the first surface 1603A (or second surface 1603B) of the segment 1601 fit together or mate, as was the situation for the segments 1301 and 1401 shown in FIGS. 13A, 13B, 14A and 14B.

Figures 17A, 17B:
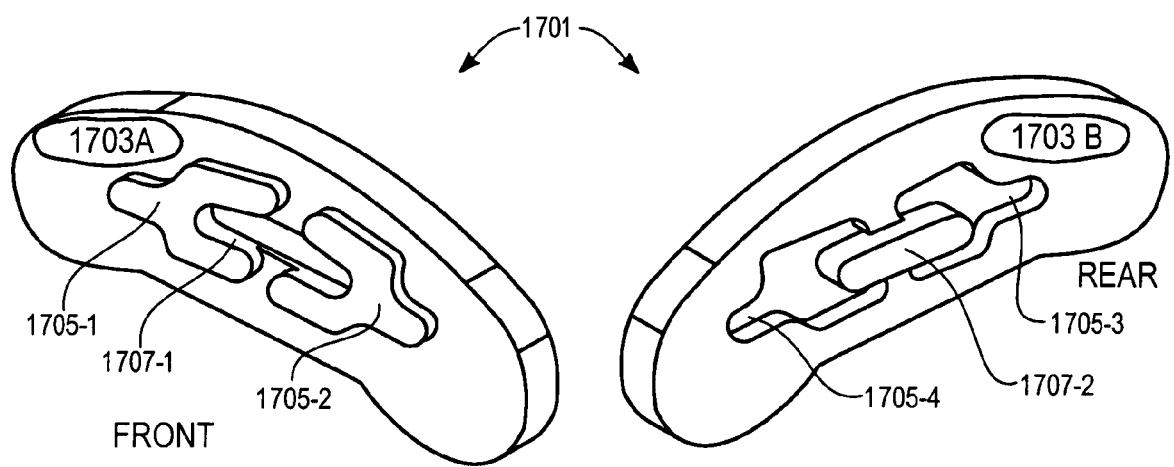

FIGS. 17A and 17B illustrate a segment 1701, having first and second surfaces, 1703A and 1703B, with complementary extensions. The first surface 1703A has two male extensions, 1705-1 and 1705-2, partly surrounding a female extension 1707-1. The second surface 1703B has two female extensions, 1705-3 and 1705-4, partly surrounding a male extension 1707-2. The male extensions, 1705-1 and 1705-2, have substantially the same shapes and sizes as the respective female extensions, 1705-3 and 1705-4; and the female extension 1707-1 has substantially the same shape and size as the male extension 1707-2. Where first and second substantially identical segments 1701 are provided, a second surface of the first segment will fit together or mate with a first surface of the second (identical) segment.

Each of the segments shown in FIGS. 13A/B, 14A/B, 15A/B, 16A/B and 17A/B relies upon a first (inner) annular sector (e.g., 1307) and a second (outer) annular sector (e.g., the combination of 1305-1 and 1305-2) on a surface of a first segment to fit together with matching annular sectors on a second segment to resist lateral, translational and rotational motion of the first segment relative to the second segment.

In FIGS. 17A/17B, for example, the first and second annular sectors on the first segment have a male extension and a female extension, respectively, or have a female extension and a male extension, respectively. The first annular sector on the second segment has a female extension (a male extension), if the first annular sector on the first segment has a male extension (a female extension). In a similar manner, the second annular sector on the second segment has a male extension (a female extension), if the second annular sector on the first segment has a female extension (a male extension). That is, the first annular sectors on the first and second segments are complementary to each other (one male extension; one female extension); and the second annular sectors on the first and second segments are also complementary to each other.

For example, where K interior segments are provided, the K-2 interior axial lengths are preferably chosen to be d(1101-2)=d, d(1101-3)=2d, d(1101-4)=4d, . . . , d(1101-(K-2))=$2^{K-3}$d, where d is a selected positive length, such as 0.5 mm or 1 mm. Two or more interior segments are arranged to lock together in any order so that any axial length d, 2d, 3d, 4d, . . . , ($2^{K-2}$-1)d can be constructed by providing one, two or more of the interior segments. This arrangement allows use of a set of two end segments (e.g., 1101-1 and 1101-4 in FIGS. 11A-11C) plus K-2 interior segments to provide any of ($2^{K-2}$-1) total axial lengths for the K-segment bone implant system, namely $$D=d(1)+h\cdot d+d(K) \; (h=0, 1, \ldots, (2^{K-2}-1)), \quad (1)$$

where d is the basic axial length of an interior segment and d(1) and d(K) are the axial lengths for the first and last (exposed) segments in the arrangement.

What is claimed is:

1. A spine implant device system for a patient, comprising:
a first implant segment, having a first selected thickness in a selected first axial direction and having at least a first annular region, a second annular region adjacent to and at least partially surrounding the first region, and a third annular region adjacent to and at least partially surrounding the second region, where at least the first region has a male extension in the first axial direction, and the second region has a female extension in the first axial direction;
a second implant segment, having a second selected thickness in a selected second axial direction and having at least a fourth annular region, a fifth annular region adjacent to and at least partially surrounding the fourth region, and a sixth annular region adjacent to and at least partially surrounding the fifth region; and
wherein at least the fourth region has a female extension in the second axial direction and the fifth region has a male extension in the second axial direction, where the first and fourth regions have a male-female interlocking relationship, and the fifth and second regions have a male-female interlocking relationship; and
wherein at least one of the third and sixth regions has a perforation channel therein that extends between an exposed surface of at least one of the first and second segments and at least one of the second and fifth regions, whereby natural bone in the patient's body is encouraged to grow into the at least one perforation channel.

2. The system of claim 1, further comprising at least one perforation channel that extends between said first segment and said second segment, whereby natural bone in the patient's body is encouraged to grow into the second perforation channel.

3. The system of claim 1, wherein said first and second axial directions are substantially parallel.

4. The system of claim 1, wherein said first axial direction has a non-zero angular offset relative to said second axial direction.

5. The system of claim 4, wherein said angular offset lies in between 0° and about 8°.

6. The system of claim 1, wherein a sum of said first and second selected thicknesses lies in a range of 5 mm to 20 mm.

7. The system of claim 1, wherein at least one of said first, third and fifth annular regions has a male extension that extends into at least one of said second, fourth and sixth female extensions by a distance lying in a range 1-7 mm.

8. The system of claim 1, wherein each of said first and fourth annular regions has a cross sectional shape, viewed transversely to at least one of said first axial direction and said second axial direction, that is substantially rectangular.

9. The system of claim 1, wherein each of said second and fifth annular regions has a cross sectional shape, viewed transversely to at least one of said first axial direction and said second axial direction, that is substantially rectangular.

10. The system of claim 1, wherein each of said third and sixth annular regions has a cross sectional shape, viewed transversely to at least one of said first axial direction and said second axial direction, that is substantially rectangular.

11. The system of claim 1, wherein at least one of said first segment and said second segment includes cortical bone as a material.

12. The system of claim 1, wherein at least one of said first segment and said second segment has first and second, spaced apart chamfered surface portions, having respective first and second chamfer planes that are substantially parallel.

13. The system of claim 1, wherein at least one of said first segment and said second segment has first, second and third, spaced apart chamfered surface portions, having respective first, second and third chamfer planes, where no two of the first, second and third chamfer planes are substantially parallel.

14. The system of claim 1, wherein said first segment first axial direction and said second segment second axial direction are oriented at a selected positive angle relative to each other.

15. The system of claim 1, wherein at least one of said first, second, third, fourth, fifth and sixth annular regions has a boundary shape that is drawn from the group of shapes consisting of ovular, polygonal and clover leaf with N sides (N 2).

16. The system of claim 1, wherein at least one of said first and second segments has a curvilinear delta cross sectional shape.

17. The system of claim 1, wherein said first implant segment and said second implant segment have respective first and second exposed surfaces that are oriented at a selected positive angle relative to each other.

18. The system of claim 1, wherein said exposed surface of at least one of said first implant segment and said second implant segment has a cross-hatched groove pattern.

19. The system of claim 1, wherein said exposed surface of at least one of said first implant segment and said second implant segment has a groove pattern that is substantially aligned in one direction.

20. The system of claim 1, wherein at least one of a top surface and a bottom surface of at least one of said first implant segment and said second implant segment has a groove pattern that is substantially aligned in one direction.

21. The system of claim 1, wherein said first implant segment has a cross sectional shape, viewed transversely to said first axial direction, that has a first selected length e1 in said axial direction, measured adjacent to said axis, has a second selected length e2 in said axial direction, measured at a positive distance from said axis, and has a third selected axial length e3, measured at an outer edge of said first implant segment, where e1<e2 and e3<e2.

22. The system of claim 1, wherein said second implant segment has a cross sectional shape, viewed transversely to said first axial direction, that has a first selected length e1 in said axial direction, measured adjacent to said axis, has a second selected length e2 in said axial direction, measured at a positive distance from said axis, and has a third selected axial length e3, measured at an outer edge of said second implant segment, where e1<e2 and e3<e2.

23. The system of claim 1,
wherein at least one of the first, second, third, fourth, fifth and sixth annular regions has at least one void therein, whereby natural bone in the patient's body is encouraged to grow into the at least one void.

24. The system of claim 23, further comprising a second void that extends between said first segment and said second segment, whereby natural bone in the patient's body is encouraged to grow into the second void.

25. The system of claim 23, wherein said first and second axial directions are substantially parallel.

26. The system of claim 23, wherein said first axial direction has a non-zero angular offset relative to said second axial direction.

27. The system of claim 23, wherein said angular offset lies between 0° and about 8°.

28. The system of claim 23, wherein a sum of said first and second selected thicknesses lies in a range of 5 mm to 20 mm.

29. The system of claim 23, wherein at least one of said first, third and fifth annular regions has a male extension that extends into at least one of said second, fourth and sixth female extensions by a distance lying in a range 1-7 mm.

30. The system of claim 23, wherein each of said first and fourth annular regions has a cross sectional shape, viewed transversely to at least one of said first axial direction and said second axial direction, that is substantially rectangular.

31. The system of claim 23, wherein each of said second and fifth annular regions has a cross sectional shape, viewed transversely to at least one of said first axial direction and said second axial direction, that is substantially rectangular.

32. The system of claim 23, wherein each of said third and sixth annular regions has a cross sectional shape, viewed transversely to at least one of said first axial direction and said second axial direction, that is substantially rectangular.

33. The system of claim 23, wherein at least one of said first segment and said second segment includes, as a material, cortical bone.

34. The system of claim 23, wherein at least one of said first segment and said second segment has first and second, spaced apart chamfered surface portions, having respective first and second chamfer planes that are substantially parallel.

35. The system of claim 23, wherein at least one of said first segment and said second segment has first, second and third, spaced apart chamfered surface portions, having respective first, second and third chamfer planes, where no two of the first, second and third chamfer planes are substantially parallel.

36. The system of claim 23, wherein said first segment first axial direction and said second segment second axial direction are oriented at a selected positive angle relative to each other.

37. The system of claim 23, wherein at least one of said first, second, third, fourth, fifth and sixth annular regions has a boundary shape that is drawn from the group of shapes consisting of ovular, polygonal and clover leaf with N sides (N 2).

38. The system of claim 23, wherein at least one of said first and second segments has a curvilinear delta cross sectional shape.

39. The system of claim 23, wherein said first implant segment and said second implant segment have respective first and second exposed surfaces that are oriented at a selected positive angle relative to each other.

40. The system of claim 23, wherein said exposed surface of at least one of said first implant segment and said second implant segment has a cross-hatched groove.

41. The system of claim 23, wherein said exposed surface of at least one of said first implant segment and said second implant segment has a groove pattern that is substantially aligned in one direction.

42. The system of claim 23, wherein at least one of a top surface and a bottom surface of at least one of said first implant segment and said second implant segment has a groove pattern that is substantially aligned in one direction.

43. The system of claim 23, wherein said first implant segment has a cross sectional shape, viewed transversely to said first axial direction, that has a first selected length e1 in said axial direction, measured adjacent to said axis, has a second selected length e2 in said axial direction, measured at a positive distance from said axis, and has a third selected axial length e3, measured at an outer edge of said first implant segment, where e1<e2 and e3<e2.

44. The system of claim 23, wherein said second implant segment has a cross sectional shape, viewed transversely to said first axial direction, that has a first selected length e1 in said axial direction, measured adjacent to said axis, has a second selected length e2 in said axial direction, measured at a positive distance from said axis, and has a third selected axial length e3, measured at an outer edge of said second implant segment, where e1<e2 and e3<e2.

45. A spine implant device system for a patient, comprising:
a first implant segment, having a first selected thickness in a selected first axial direction and having at least a first annular region and a second annular region, adjacent to and at least partly surrounding the first region, where one of the first and second annular regions has a male extension and the other of the first and second annular regions has a female extension, in the first axial direction;

a second implant segment, having a second selected thickness in a selected second axial direction and having at least a third annular region and a fourth annular region, adjacent to and at least partly surrounding the third annular region; and wherein one of the third and fourth annular regions has a male extension and the other of the third and fourth annular regions has a female extension, in the second axial direction, that are complementary to the first annular region and to the second annular region, respectively, so that the first and third annular regions have a male-female interlocking relationship and the second and fourth annular regions have a male-female interlocking relationship.

46. The system of claim 45, further comprising at least one perforation channel that extends between said first segment and said second segment, whereby natural bone in the patient's body is encouraged to grow into the second perforation channel.

47. The system of claim 45, wherein said first and second axial directions are substantially parallel.

48. The system of claim 45, wherein said first axial direction has a non-zero angular offset relative to said second axial direction.

49. The system of claim 45, wherein said angular offset lies between 0° and about 8°.

50. The system of claim 45, wherein a sum of said first and second selected thicknesses lies in a range of 5 mm to 20 mm.

51. The system of claim 45, wherein at least one of said first and second annular regions of said first segment has a male extension that extends into at least one female of said first and second annular regions of said second segment by a distance lying in a range 1-7 mm.

52. The system of claim 45, wherein each of said first annular region of each of said first segment and said second segment has a cross sectional shape, viewed transversely to at least one of said first axial direction and said second axial direction, that is substantially rectangular.

53. The system of claim 45, wherein each of said second annular region of each of said first segment and said second segment has a cross sectional shape, viewed transversely to at least one of said first axial direction and said second axial direction, that is substantially rectangular.

54. The system of claim 45, wherein at least one of said first segment and said second segment includes cortical bone as a material.

55. The system of claim 45, wherein at least one of said first segment and said second segment has first and second, spaced apart chamfered surface portions, having respective first and second chamfer planes that are substantially parallel.

56. The system of claim 45, wherein at least one of said first segment and said second segment has first, second and third, spaced apart chamfered surface portions, having respective first, second and third chamfer planes, where no two of the first, second and third chamfer planes are substantially parallel.

57. The system of claim 45, wherein said first segment first axial direction and said second segment second axial direction are oriented at a selected positive angle relative to each other.

58. The system of claim 45, wherein at least one of said first and second segments has a curvilinear delta cross sectional shape.

59. The system of claim 45, wherein said first implant segment and said second implant segment have respective first and second exposed surfaces that are oriented at a selected positive angle relative to each other.

60. The system of claim 45, wherein said exposed surface of at least one of said first implant segment and said second implant segment has a cross-hatched groove.

61. The system of claim 45, wherein said exposed surface of at least one of said first implant segment and said second implant segment has a groove pattern that is substantially aligned in one direction.

62. The system of claim 45, wherein at least one of a top surface and a bottom surface of at least one of said first implant segment and said second implant segment has a groove pattern that is substantially aligned in one direction.

63. The system of claim 45, wherein said first implant segment has a cross sectional shape, viewed transversely to said first axial direction, that has a first selected length e1 in said axial direction, measured adjacent to said axis, has a second selected length e2 in said axial direction, measured at a positive distance from said axis, and has a third selected axial length e3, measured at an outer edge of said first implant segment, where e1<e2 and e3<e2.

64. The system of claim 45, wherein said second implant segment has a cross sectional shape, viewed transversely to said first axial direction, that has a first selected length e1 in said axial direction, measured adjacent to said axis, has a second selected length e2 in said axial direction, measured at a positive distance from said axis, and has a third selected axial length e3, measured at an outer edge of said second implant segment, where e1<e2 and e3<e2.

* * * * *